(12) United States Patent
Cull

(10) Patent No.: US 6,752,795 B2
(45) Date of Patent: Jun. 22, 2004

(54) ADJUSTABLE FLUID FLOW RESISTOR CASSETTE

(75) Inventor: Laurence J. Cull, Wildwood, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 176 days.

(21) Appl. No.: 10/179,640

(22) Filed: Jun. 24, 2002

(65) Prior Publication Data

US 2003/0236508 A1 Dec. 25, 2003

(51) Int. Cl.[7] .......................... A61M 1/00; F16K 47/00; F16L 55/02
(52) U.S. Cl. ...................... 604/323; 604/246; 604/537; 604/294; 251/127
(58) Field of Search ................ 604/246–299, 604/537, 294–302, 323; 251/121, 127, 126; 138/42, 43, 46

(56) References Cited

U.S. PATENT DOCUMENTS

| | | | | |
|---|---|---|---|---|
| 688,836 A | * | 12/1901 | Diehl | 126/296 |
| 1,200,816 A | * | 10/1916 | Cox | 110/146 |
| 2,032,623 A | * | 3/1936 | Lewis | 251/161 |
| 3,312,249 A | * | 4/1967 | Cadiou | 138/42 |
| 3,957,083 A | * | 5/1976 | Gallo | 138/43 |
| 4,105,162 A | * | 8/1978 | Drori | 239/109 |
| 4,364,415 A | * | 12/1982 | Polon | 137/625.32 |
| 4,460,129 A | * | 7/1984 | Olson | 239/542 |
| 4,887,522 A | * | 12/1989 | Kuno et al. | 454/309 |
| 5,019,054 A | * | 5/1991 | Clement et al. | 604/248 |
| 5,111,996 A | * | 5/1992 | Eckstein | 239/542 |
| 5,364,303 A | * | 11/1994 | Terry | 454/155 |
| 5,484,402 A | * | 1/1996 | Saravia et al. | 604/35 |
| 5,524,863 A | * | 6/1996 | Davis | 251/127 |
| 5,565,063 A | * | 10/1996 | Begemann et al. | 162/216 |
| 5,615,708 A | * | 4/1997 | Barron | 137/625.3 |
| 5,680,889 A | * | 10/1997 | Boger | 137/625.32 |
| 5,697,403 A | * | 12/1997 | Onishi et al. | 138/37 |
| 5,800,408 A | * | 9/1998 | Strauss et al. | 604/264 |
| 5,829,246 A | * | 11/1998 | Abrams et al. | 60/761 |
| 5,988,586 A | * | 11/1999 | Boger | 251/127 |
| 6,029,702 A | * | 2/2000 | Leinen et al. | 137/625.32 |
| 6,089,539 A | * | 7/2000 | Kouda | 251/149.2 |
| 6,106,498 A | * | 8/2000 | Friedli et al. | 604/153 |
| 6,254,576 B1 | * | 7/2001 | Shekalim | 604/246 |
| 6,269,704 B1 | * | 8/2001 | Ziv et al. | 73/863.84 |
| 6,378,558 B1 | * | 4/2002 | Pohl et al. | 137/827 |
| 6,491,053 B1 | * | 12/2002 | Briggeman et al. | 137/13 |
| 6,682,503 B1 | * | 1/2004 | Fariss et al. | 604/34 |
| 2003/0236530 A1 | * | 12/2003 | Cull et al. | 606/107 |
| 2004/0000349 A1 | * | 1/2004 | Cull et al. | 138/42 |

* cited by examiner

*Primary Examiner*—John J. Calvert
*Assistant Examiner*—Michael G Bogart
(74) *Attorney, Agent, or Firm*—Michael L. Smith

(57) ABSTRACT

An adjustable fluid flow resistor cassette 10 for use in ophthalmic surgery, includes a housing 12. A set of path restrictors 24 are disposed within the housing 12, and the restrictors 24 cooperate to vary a fluid flow path length from an inlet 16 to an outlet 18.

14 Claims, 3 Drawing Sheets

ADJUSTABLE FLUID FLOW RESISTOR CASSETTE

BACKGROUND OF THE INVENTION

1. Field of the Invention

The present invention is related to devices for restricting the flow of aspirant during surgery, especially ophthalmic surgery. In particular, the present invention relates to devices that are adjustable so as to provide a range of aspirant flow resistance and are incorporated into a surgical fluid collection cassette.

2. Description of Related Art

During eye surgery, especially cataract surgery, surgeons experience a tension between the amount of vacuum or aspiration to be used on a patient's eye and the time period in which the surgeon has to respond to events that may occur during surgery. Surgeons typically prefer higher vacuum levels to provide a higher holding force for the cataract. However, these higher vacuum levels result in the need for rapid response times by the surgeon when events such as occlusion occur in the aspiration line. The higher the vacuum levels, the quicker events occur and thus the potential for serious problems increases, such as the tearing of the capsular bag.

There are known devices for increasing the resistance to aspirant fluid flow to allow a surgeon to use higher vacuum levels, i.e., higher holding force, with a slower response time. These devices help the surgeon have the benefits of higher vacuum levels while limiting or minimizing the risks by providing the surgeon with greater time to respond to surgical events than would be possible without resistance to the aspirant flow. Coiled tubing is one example that increases the flow resistance. It has been asserted that increased resistance is achieved by passing fluid through a series of coil bends because fluid drops in pressure as it flows through a bend. However, a downside to the coiled tubing is that the chances of aspirant clogging within the coils is increased due to the elliptical cross-section and bent kinks that may occur in the tubing. In addition, the resistance of the coiled tubing is a function of the coil radius and the resistance cannot be varied during surgery.

Another device that increases resistance to aspirant flow is a non-clogging orifice that collects waste and is commonly referred to phaco-guard. The phaco-guard is a large cross-sectional area filter funneled down to a small orifice. It allows limited clogging of the filter and is based on the assumption that the entire filter area will not clog. The filter may still clog and it is not adjustable.

Therefore, it would be advantageous to have a fluid flow resistor that is adjustable to provide the surgeon with a range of aspirant flow resistance.

It would be further advantageous to incorporate the fluid flow resistor into a aspirant fluid collection cassette to reduce the number of devices needed by a surgeon, and also to easily allow automation or motorization of the resistance adjustment.

DETAILED DESCRIPTION OF THE PREFERRED EMBODIMENT

Figure 1:
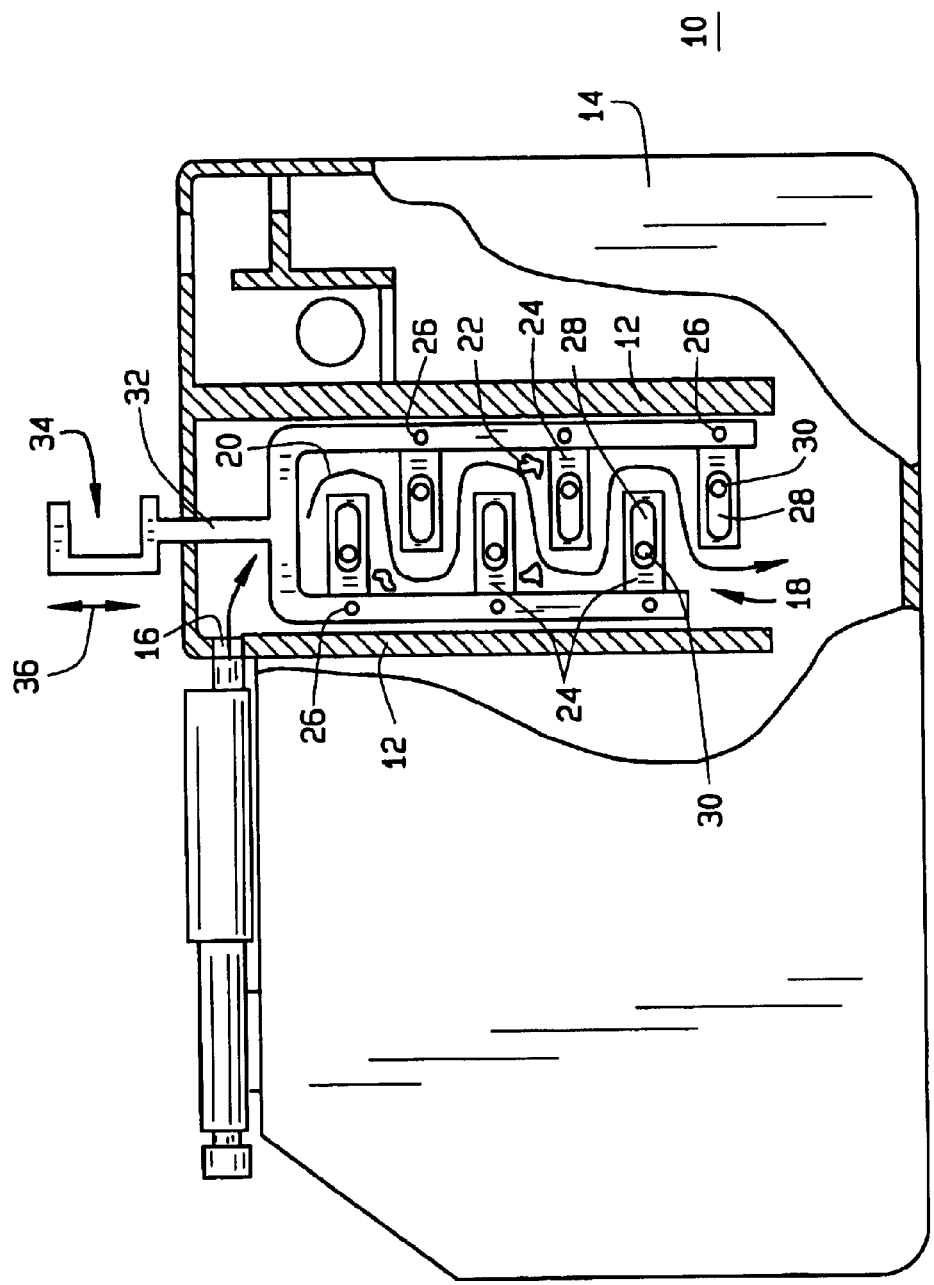
FIG. 1 is a partial cut-away elevation of a cassette in accordance with the present invention, shown in a position of maximum flow resistance.

An adjustable fluid flow resistor cassette 10 for use in ophthalmic surgery is shown in FIG. 1. A housing 12 is formed in or by a portion of a surgical fluid collection cassette 14. The housing 12 has an inlet 16 and an outlet 18 for receiving a flow of aspirant fluid from a surgical site, wherein the fluid flows from the inlet 16 to the outlet 18 along line 20. The aspirant fluid typically contains bits of tissue, such as cataract material 22 that has been removed during eye surgery. A set of path restrictors 24 are disposed within the housing 12 between the inlet 16 and outlet 18, such that the path restrictors 24 cooperate to vary a fluid flow path length shown by line 20, from the inlet 16 to the outlet 18. Aspirant fluid flow resistance increases as the path length 20 increases from the inlet 16 to the outlet 18. Cassette 10 is preferably otherwise the same as cassettes found in the prior art, such as those available from Bausch & Lomb Incorporated for use in its Millennium™ Surgical System.

The set of path restrictors 24 are preferably a plurality of interspersed fingers hinged at 26 within the housing 12, such that the fingers move in unison to vary the path length. The restrictors 24 preferably include slots 28, which contain pins 30 to define a pivot path for restrictors 24. Preferably, the path restrictors include at least two (2) fingers and preferably six (6) as shown in FIG. 1. Obviously, the more interspersed fingers, the greater the path length attainable, and thus the greater the aspirant fluid flow resistance that may be achieved.

Preferably, the path restrictors 24 are attached to a handle 32, which causes movement of the path restrictors 24, and thereby varies the path length. Preferably, handle 32 includes structure such as shown at 34 to cooperate with a motorized mechanism of a surgical console such as described below to vary the path length. Handle 32 can also be moved manually by a user, by moving the handle 32 as indicated by arrow 36.

Obviously a cross-section of the path defined by line 20 is at least as large as an inner-diameter of a distal end of a surgical handpiece to be connected to the cassette 14 so that the aspirant fluid may flow freely from the inlet 16 to the outlet 18 without clogging. It is preferred that the path restrictors form a path that causes turbulent fluid flow. Turbulent flow is known to have higher resistance than laminar flow.

Figure 2:
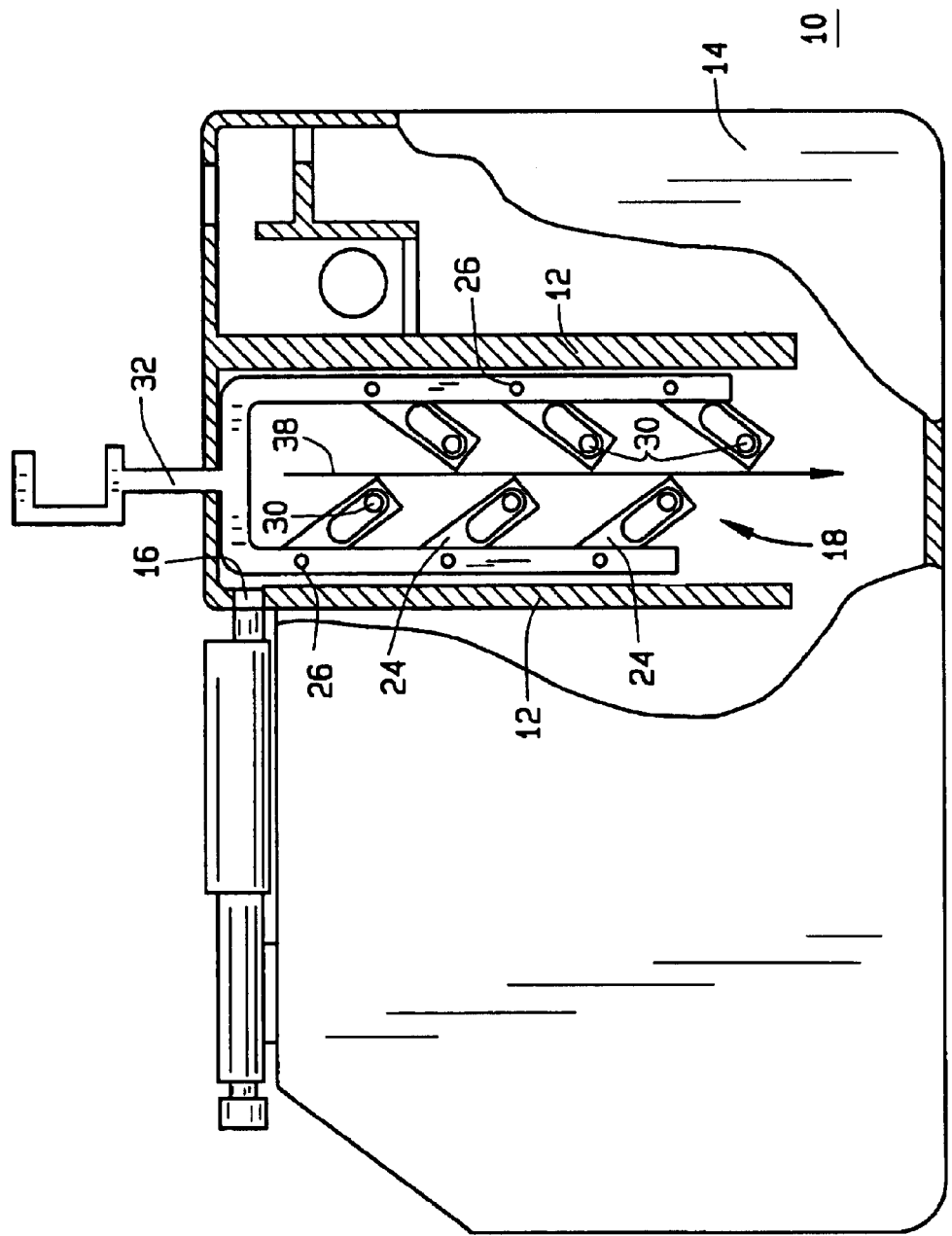
FIG. 2 is a partial cut-away elevation of a cassette in accordance with the present invention, shown in a position of least flow resistance.
Figure 3:
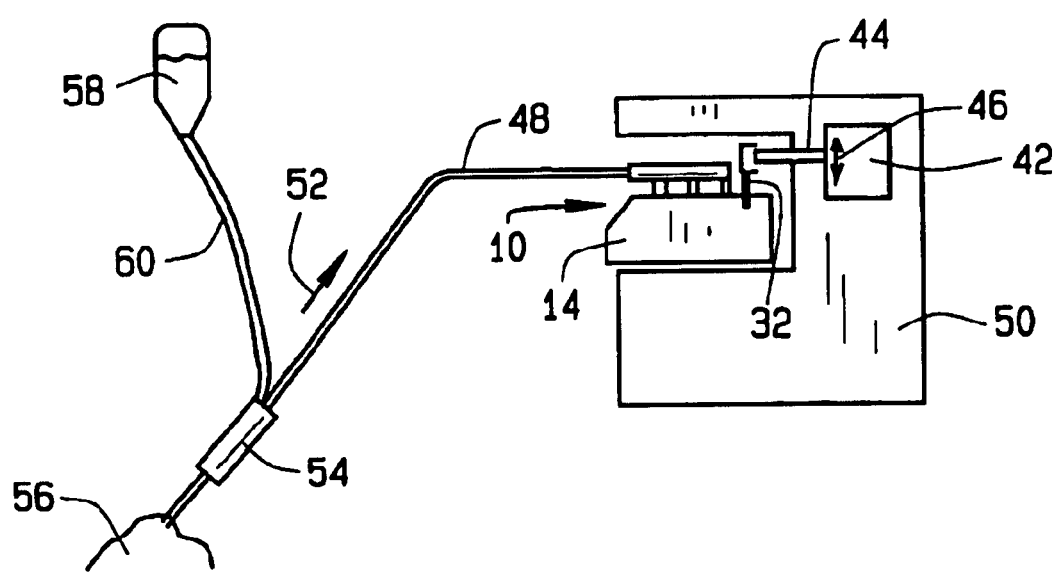
FIG. 3 is a diagram of a cassette in accordance with the present invention being used during ophthalmic surgery.

FIG. 2 discloses the cassette 10 in a position of minimum resistance as opposed to the maximum resistance position shown in FIG. 1. In operation, the plurality of interspersed fingers 24 hinged within housing 12 move in unison to vary a fluid path length from the inlet 16 to the outlet 18. The handle 32, attached to the fingers or restrictors 24, move about their respective hinges 26 so that as the path length increases the aspirant fluid flow resistance increases. The aspirant flow path is shown at a minimum at line 38. An ophthalmic surgical system 40 as shown in FIG. 3, includes a cassette 14 with handle 32 coupled to motorized mechanism 42, which moves arm 44 in the direction of arrow 46 to move the handle 32, and thereby vary the path length. Cassette 14 connected to aspirant tubing 48 in surgical console 50 causes aspirant to flow in the direction of arrow 52 from handpiece 54, which is performing a surgical operation on eye 56. As is well-known in the art, irrigation fluid 58 is fed to eye 56 through tubing 60.

While there has been shown and described a particular embodiment of an adjustable fluid flow resistor incorporated into a cassette, other embodiments of an adjustable fluid flow resistor may be incorporated into a cassette without departing from the scope of the present invention. Particularly, the fluid flow resistor may include a resistor of similar construction to that described in co-pending patent application "Adjustable Fluid Flow Resistor", serial number (to be assigned), and which is incorporated herein by reference.

I claim:

1. An adjustable fluid flow resistor cassette for use in ophthalmic surgery comprising:
    a housing formed in a portion of a surgical fluid collection cassette wherein the housing has an inlet and an outlet for receiving a flow of aspirant fluid from a surgical site wherein the fluid flows from the inlet to the outlet;
    a set of path restrictors disposed within the housing and between the inlet and outlet such that at least some of the path restrictors cooperate to vary a fluid flow path length from the inlet to the outlet; and
    wherein an aspirant fluid flow resistance increases as the path length increases from the inlet to the outlet.

2. The cassette of claim 1 wherein the set of path restrictors is a plurality of interspersed fingers hinged within the housing such that at least some of the fingers move in unison to vary the path length.

3. The cassette of claim 2 wherein the path restrictors include at least two (2) fingers.

4. The cassette of claim 1 wherein the path restrictors are attached to a handle for causing movement of at least some of the path restrictors thereby varying the path length.

5. The cassette of claim 4 wherein the handle cooperates with a motorized mechanism of a surgical console to vary the path length.

6. The cassette of a claim 1 wherein a cross-section of the path is at least as large as an inner-diameter of a distal end of a surgical handpiece to be connected to the cassette so that aspirant fluid may flow freely from the inlet to the outlet.

7. An adjustable fluid flow resistor cassette for use in ophthalmic surgical comprising:
    a housing formed by a portion of a surgical fluid collection cassette wherein the housing has an inlet and an outlet for receiving a flow of aspirant fluid from a surgical site wherein the fluid flows from the inlet to the outlet;
    a plurality of interspersed fingers hinged within the housing such that at least some of the fingers move in unison to vary a fluid flow path length from the inlet to the outlet; and
    a handle attached to the fingers such that when the handle is moved the fingers move about their respective hinges such that as the path length increases an aspirant fluid flow resistance increases.

8. The cassette of claim 7 wherein there are at least two (2) fingers.

9. The cassette of claim 7 wherein the handle cooperates with a motorized mechanism of a surgical console to vary the path length.

10. The cassette of a claim 7 wherein a cross-section of the path is at least as large as an inner-diameter of a distal end of a surgical handpiece to be connected to the cassette so that aspirant fluid may flow freely from the inlet to the outlet.

11. An ophthalmic surgery system comprising:
    a surgical fluid collection cassette;
    an ophthalmic surgical console for controlling a surgical handpiece and retaining the cassette;
    a housing formed by a portion of the cassette wherein the housing has an inlet and an outlet for receiving a flow of aspirant fluid from a surgical site wherein the fluid flows from the inlet to the outlet;
    a set of path restrictors disposed within the housing and between the inlet and outlet such that at least some of the path restrictors cooperate to vary a fluid flow path length from the inlet to the outlet such that an aspirant fluid flow resistance increases as the path length increases;
    a handle attached to the set of path restrictors for causing movement of at least some of the restrictors thereby varying the path length; and
    a motorized mechanism of the surgical console that couples to the handle to move the handle and thereby vary the path length.

12. The cassette of claim 11 wherein the set of path restrictors is a plurality of interspersed fingers hinged within the housing such that at least some of the fingers move in unison to vary the path length.

13. The cassette of claim 11 wherein the path restrictors include at least two (2) fingers.

14. The cassette of a claim 11 wherein a cross-section of the path is at least as large as an inter-diameter of a distal end of a surgical handpiece to be connected to the cassette so that aspirant fluid may flow freely from the inlet to the outlet.

* * * * *